United States Patent
Warner et al.

(10) Patent No.: US 9,615,762 B2
(45) Date of Patent: Apr. 11, 2017

(54) COORDINATING INTERFACE FOR ELECTROPHYSIOLOGY STUDIES

(71) Applicant: General Electric Company, Schenectady, NY (US)

(72) Inventors: Adrian F. Warner, Wauwatosa, WI (US); Claudio Patricio Mejia, Wauwatosa, WI (US); Daniel Richard Schneidewend, Wauwatosa, WI (US); Roger F Schmit, Wauwatose, WI (US); Timothy P Stiemke, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 148 days.

(21) Appl. No.: 14/566,873

(22) Filed: Dec. 11, 2014

(65) Prior Publication Data

US 2016/0166171 A1 Jun. 16, 2016

(51) Int. Cl.
*A61B 5/0428* (2006.01)
*A61B 18/12* (2006.01)
*A61B 5/04* (2006.01)
*A61B 5/042* (2006.01)

(52) U.S. Cl.
CPC .......... *A61B 5/04288* (2013.01); *A61B 18/12* (2013.01); *A61B 5/04017* (2013.01); *A61B 5/0422* (2013.01)

(58) Field of Classification Search
CPC combination set(s) only.
See application file for complete search history.

(56) References Cited

U.S. PATENT DOCUMENTS

| | | | |
|---|---|---|---|
| 5,467,090 A * | 11/1995 | Baumgartner | A61B 5/0428 341/139 |
| 5,699,808 A | 12/1997 | John | |
| 5,720,294 A | 2/1998 | Skinner | |
| 5,813,991 A | 9/1998 | Willis et al. | |
| 6,950,697 B2 | 9/2005 | Jordan | |
| 7,549,959 B2 | 6/2009 | Takala et al. | |
| 7,881,778 B2 | 2/2011 | Rantala | |
| 8,041,418 B2 | 10/2011 | Giftakis et al. | |
| 2005/0101875 A1* | 5/2005 | Semler | A61B 5/04085 600/509 |
| 2005/0165323 A1 | 7/2005 | Montgomery et al. | |

(Continued)

OTHER PUBLICATIONS

"Neuro-Cardiogenic Syncope Patent Information", Northwest Ohio Cardiology Consultants, Mar. 2001, 2 pages.

(Continued)

*Primary Examiner* — Kabir A Timory
(74) *Attorney, Agent, or Firm* — Boyle Fredrickson, S.C.

(57) ABSTRACT

A coordinating interface for electrophysiological signals provides inputs for ECG and intra-cardiac electrodes and provides a computer controllable processing path outputting data using a shareable digital data output. Requests received over a digital control line allow the computer to control a multiway switch and analog filter set to arbitrate among different uses of the electrophysiological signals by different devices. A single coordinating interface helps reduce interference from competing uses. Pre-stored configuration data simplifies the connection of different devices having different uses of the physiological data.

21 Claims, 2 Drawing Sheets

(56) References Cited

U.S. PATENT DOCUMENTS

2006/0020218 A1* 1/2006 Freeman ............... A61B 5/04
600/509
2012/0109242 A1 5/2012 Levin et al.

OTHER PUBLICATIONS

Grubb, "Neurocardiogenic Syncope and Related Disorders of Orthostatic Intolerance", http://www.circulationaha.org, Sep. 14, 2004, 11 pages.
Samuels. "Neurogenic heart disease: a unifying hypothesis", Am J. Cardiol, Dec. 28, 1987; 60(18):15J-19J, Abstract Only.
Samuels, "Neurally induced cardiac damage. Definition of the problem.", Neuol Clin. May 1993; 11(2); 273-92, Abstract Only.

* cited by examiner

COORDINATING INTERFACE FOR ELECTROPHYSIOLOGY STUDIES

STATEMENT REGARDING FEDERALLY SPONSORED RESEARCH OR DEVELOPMENT

Not Applicable

CROSS REFERENCE TO RELATED APPLICATION

Not Applicable

BACKGROUND OF THE INVENTION

The present invention relates to electronic equipment for electrophysiology studies and in particular to an interface for electrophysiology devices that reduces interference and conflict among the electrophysiology devices.

Electrophysiology studies provide complex measurements of the electrical activity and conduction pathways of the heart that may be used, for example, to analyze and treat heart arrhythmias. An example study may use multiple surface ECG electrodes applied to the patient's skin together with intra-cardiac electrodes inserted into the patient's heart and monitoring electrical activity directly on the muscle wall of the heart. Electrical stimulation may be applied to the heart muscle through an intra-cardiac pacing electrodes to promote heart action that may be monitored. An intra-cardiac ablation electrode may be used to burn tissue of the heart to alter heart conduction pathways in a manner that may reduce or stop arrhythmia. A mapping device may use signals from a catheter in the heart, for example, providing an insertion path for intra-cardiac electrodes or one of the intra-cardiac electrodes to locate the position of the intra-cardiac electrodes.

In an electrophysiology study, multiple devices must have access to electrical signals from the body. Those devices typically include an ECG monitor for monitoring patient heartbeat, a stimulator device for providing pacing signals to the heart through one or more intra-cardiac electrodes, an intra-cardiac signal-recording device recording signals from the intra-cardiac electrodes, a mapping device determining a location of the intra-cardiac electrodes, and an ablation circuit providing ablative power through one or more of the intra-cardiac electrodes. Other devices such as x-ray equipment may also require access to these electrical signals, for example, for the purpose of gating image data to particular physiological activity such as respiration or cardiac cycle.

As a practical matter, these multiple devices must share limited electrode resources either in the form of discrete electrodes or practical locations for electrodes. Electrically sharing individual electrodes can generate cross-coupled noise between devices, problems with ground stabilization, and direct interference from conflicting uses, for example, between ablation or pacing and the measurement of sensitive physiological signals. Competing and different filtration requirements can make shared electrodes impractical in many cases and substantially increase the amount of time setting up and troubleshooting circuit paths in the operating room.

SUMMARY OF THE INVENTION

The present invention provides a coordinating interface for multiple electrophysiology signals that permits limited electrode resources to be subject to a computer-mediated arbitration between competing devices. By creating a single, versatile interface that may receive and process signals to and from the patient for multiple devices, competing leads and incompatible uses may be intelligently reconciled.

Specifically, in one embodiment, the invention provides an interface for electrophysiological signals having a set of electrode electrical connectors adapted to connect to electrical leads communicating between a patient and the interface and an analog-to-digital converter system providing multiple independent analog-to-digital converters. A computer controllable multiway switch connects signals from different ones of the electrical connectors to different inputs of different analog-to-digital converters according to a computer signal for conversion of analog signals from the electrical connectors to digital signals. A data network receives the digital signals and provides connectors adapted to connect the digital signals to medical devices requiring electrical signals from given sets of electrode electrical connectors. In addition, a control network system receives requests from at least two given medical devices describing needed electrical signals from the set of electrode electrical connectors. An electronic computer communicates with the control network system and executes a program stored in non-transitory medium to receive the requests from the given medical devices and arbitrate among the requests to provide the computer signal to the computer controllable multiway switch to connect the given medical devices through the multiway switch to selected electrodes of the set of electrode electrical connectors.

It is thus a feature of at least one embodiment of the invention to provide intelligent arbitration between competing demands of different medical devices for limited electrode resources. By computerizing this arbitration, simplified connection to the patient may be made while maximizing the availability of the electrodes and minimizing interference and the need for manual reconfiguration.

The data network and/or the control network may provide a serial communication protocol such as but not limited to Ethernet or USB. It is thus a feature of at least one embodiment of the invention to provide a simple, scalable method of communicating with multiple medical devices needing electrode data amenable to computer arbitration.

The data network and/or the control network may employ an optical fiber link.

It is thus a feature of at least one embodiment of the invention to provide communication among multiple different medical devices that eliminated unwanted leakage currents.

The interface may further include a computer controllable filter array providing frequency filtering to signals received from the electrode electrical connectors and positioned between the electrode electrical connectors and the analog-to-digital converter system, the computer control filter array communicating with the electronic computer and providing multiple independent filters having frequency profiles selectable by the electronic computer.

It is thus a feature of at least one embodiment of the invention to permit each medical device to flexibly receive different types of filtration depending on the intended use and the other contemporaneous uses.

The multiple independent filters may operate in either the analog or digital domain.

It is thus a feature of at least one embodiment of the invention to pre-attenuate electrical noise to permit accurate analog-to-digital conversion.

The interface for electrophysiological signals includes a monitor output terminal connectable to an ECG monitor receiving output directly from the independent filters without analog-to-digital conversion.

It is thus a feature of at least one embodiment of the invention to permit direct connection of standardized ECG signals that do not need significant manipulation directly to an external medical device.

The interface may further include computer-controllable bypass switches having input terminals connectable to sources of electrical power and outputs connected to ones of the electrode electrical connectors, the bypass switches communicating with the electronic computer to be closed or opened by signals from the electronic computer.

It is thus a feature of at least one embodiment of the invention to permit the interface not only of received physiological signals but also of transmitted pacing and stimulation signals.

The bypass switches may be electromechanical relays or solid state devices

It is thus a feature of at least one embodiment of the invention to provide extremely low-impedance bypass connections for high-power conduction.

The interface may further include signal sensors positioned in series along an electrical path between the input terminals connectable to sources of electrical power and those sources of electrical power for providing monitoring signals to the analog-to-digital converter system.

It is thus a feature of at least one embodiment of the invention to permit accurate monitoring of stimulation and/or pacing signals for diagnostics or fault detection.

The interface may further include a right leg drive circuit for providing a drive current to one of the electrode electrical connectors connectable to a ground pad and receiving signals from the data network to determine the drive current.

It is thus a feature of at least one embodiment of the invention to provide a right leg drive circuit that may use the flexible structure of the interface for improved ground-level sensing.

The requests for electrode resources received by the electronic computer may be associated with priorities and the arbitration provides the computer signals according to the priority so that the multiway switch selects the electrodes of the set of electrode electrical connectors required for the request of highest priority.

It is thus a feature of at least one embodiment of the invention to permit automatic arbitration based on predetermined priorities.

The arbitration may allow simultaneous service of requests of different priority that do not require conflicting settings of the multiway switch.

It is thus a feature of at least one embodiment of the invention to intelligently maximize the use of limited electrode resources.

The priorities may be stored in non-transitory medium indexed to a particular medical device and the requests may identify the medical device.

It is thus a feature of at least one embodiment of the invention to provide a simple method of assigning priorities according to the medical device.

Alternatively or in addition, the non-transitory medium may be indexed to a particular process of a particular medical device and the requests may identify the medical device and the process of the medical device.

It is thus a feature of at least one embodiment of the invention to permit a process level of granularity in assigning priorities.

The requests may identify a particular process and the device data structure may link processes to process duration and the arbitration grants priority to a given process for the duration in the data structure.

It is thus a feature of at least one embodiment of the invention to prevent allocation "starvation" of low-priority devices by limiting process duration.

The requests may identify a particular process, and the non-transitory medium may hold a configuration data structure linking processes to configurations, and the electronic computer may execute the program to receive requests identifying a particular process and use the configurations from the configuration data structure to provide the computer signal to the computer controllable multiway switch.

It is thus a feature of at least one embodiment of the invention to accommodate a variety of different interface configurations by permitting automatic reconfiguration of the interface according to its current use.

The configuration data structure may provide configurations identifying a given sets of electrode electrical connectors according to functions of associated electrodes, and the non-transitory medium further includes a lead function table relating electrode electrical connectors to particular lead functions, and the electronic computer may execute the program to compare the configurations against the lead functions per the lead function table. For example, the functions may include the functions of: ECG electrode, intra-cardiac electrode, stimulating electrode, and pacing electrode.

It is thus a feature of at least one embodiment of the invention to simplify configuration of the interface by allowing identification of electrodes by function rather than, say, by connector number.

The interface may include at least one digital-to-analog converter communicating with the data network to provide an output signal derived from at least one of the signals received by the electrode electrical connectors.

It is thus a feature of at least one embodiment of the invention to provide an output for legacy devices that can not receive the digital network signal.

The interface may further include a multiplexer for multiplexing an output of the independent analog-to-digital converters to the data network.

It is thus a feature of at least one embodiment of the invention to provide a simple reduced media connection to multiple medical devices through the use of a multiplexed digital signal.

These particular objects and advantages may apply to only some embodiments falling within the claims and thus do not define the scope of the invention.

DETAILED DESCRIPTION OF THE PREFERRED EMBODIMENT

Figure 1:
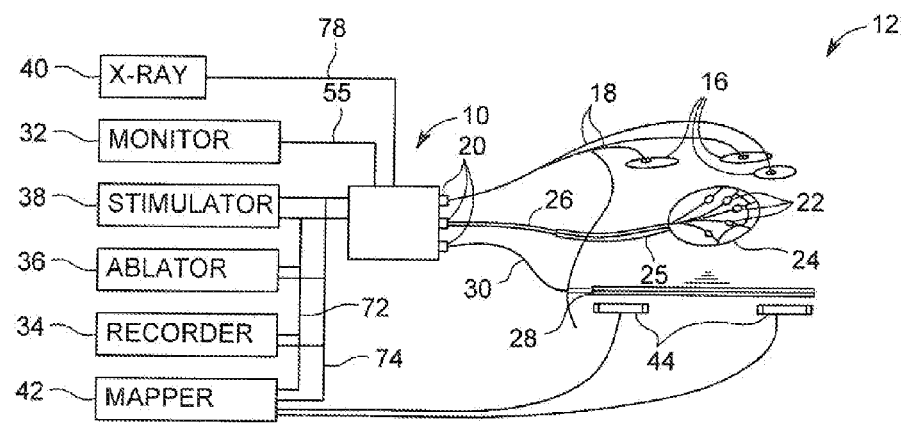
FIG. 1 is a simplified block diagram of the interface of the present invention positioned between the patient and multiple medical devices.

Referring now to FIG. 1, the coordinating interface 10 of the present invention may provide a gateway between a patient 12 and multiple medical devices 14 including those related to electrophysiology.

In one example, the patient 12 may have multiple surface ECG electrodes 16 communicating via surface ECG leads 18 to input connectors 20 on the interface 10. Intra-cardiac electrodes 22, introduced within the heart 24 of the patient by a catheter 25, may also communicate with connectors 20 communicating via intra-cardiac leads 26. The intra-cardiac electrodes 22 may include sensing electrodes as well as stimulating and pacing electrodes. A ground pad electrode 28 may also communicate with connectors 20 via leads 30.

The medical devices 14 may include, for example, a monitor 32 providing for visual display and automatic monitoring of the signals from the surface ECG electrodes 16 and intra-cardiac electrodes 22. The medical devices 14 may also include a recorder unit 34 synchronously recording ECG signals from surface ECG electrodes 16 and intra-cardiac electrodes 22, an ablation unit 36 providing ablative current flow to an intra-cardiac electrode 22 for burning or scarring muscle tissue, a stimulator 38 for providing an electrical pacing signal to an intra-cardiac electrode 22 for the purpose of generating particular heart activity or response, and a medical imaging device such as an x-ray machine 40 using electrophysiological signals to produce gated images of the heart 24 timed to particular physiological periods such as a heartbeat or respiration cycle. One medical device 14 may be a mapping unit 42 that may receive signals from the surface ECG electrodes 16 and/or the intra-cardiac electrodes 24 and apply signals to the intra-cardiac electrodes to track their position via localizing antennas 44. An example mapping unit 42 suitable for use with the present invention is manufactured by Biosensor Webster under the trade name Carto3® and employs technology described in U.S. Pat. No. 5,813,991 hereby incorporated by reference.

Figure 2:
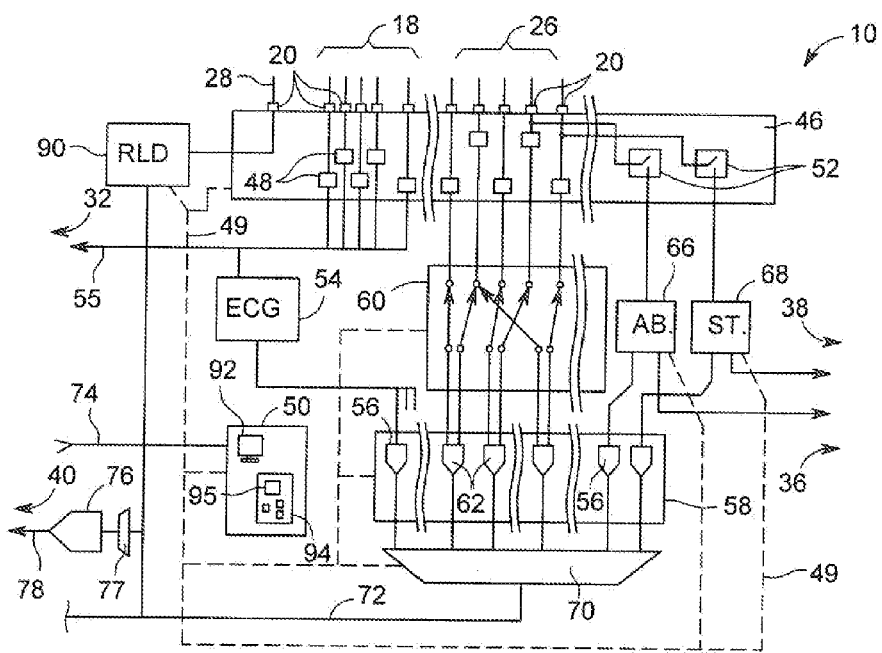
FIG. 2 is a detailed block diagram of the interface showing its principal functional circuits under the control of a programmable computer element.

Referring now to FIG. 2, ECG signals from surface ECG leads 18 and intra-cardiac signals from intra-cardiac leads 26 may be received by a switch/filter circuit 46 providing a set of independent electronically configurable filter blocks 48. The filter blocks 48 may implement a variety of different filter configurations including, for example, high pass, low pass, band rejection and band pass filters with settable frequency points. These filters may be used to reduce interference, for example, from external noise sources or from other medical devices 14, for example, from the pacing signals from stimulator 38 or from the ablation signal from ablation unit 36. These filters may be implemented in the analog domain so as to be able to handle a wide dynamic range outside of that typically available in an analog-to-digital converter; however, suitable gain control and digital filter solutions may also be provided. The filter settings may be controlled by a central controller 50 communicating with the switch/filter circuit 46 by a control line 49.

The ECG signals from surface ECG leads 18, after passing through the filter blocks 48 controlled by the controller 50, may be received by ECG processing circuit 54. The ECG processing circuit 54 may apply, for example, additional signal processing to the signals, for example, removing respiration artifacts or the like, as is understood in the art, and may provide additional filtering unique to standard ECG recording. The ECG processing circuit 54 may provide standard 12-lead ECG signals.

The ECG signals from the surface ECG leads 18, after passing through the filter blocks, 48 may be provided directly to the monitor 32 in analog form on signal wire 55 for monitors 32 that expect analog signals. Typically the monitors 32 will provide processing circuitry similar to that of ECG processing circuit 54. Because the signals from the surface ECG leads 18 are relatively standardized they may be treated separately from the intra-cardiac leads 26.

In addition, the output of the ECG processing circuit 52 may be received by multiple analog-to-digital converters 56 of a multiple analog-to-digital converter bank 58. For example, each analog-to-digital converter 56 may receive and process one ECG lead.

Generally, analog-to-digital converter bank 58 provides a number of different analog-to-digital converters including single input analog-to-digital converters 56 and differential analog-to-digital converters 62, the latter of which convert a difference signal at their inputs into a digital output. It will be appreciated that multiple analog-to-digital converter functions are required but these may be implemented by discrete independent circuits or by a single or limited number of high-speed analog-to-digital converters multiplexed among inputs and outputs which shall be considered herein as equivalent to multiple analog-to-digital converters.

The intra-cardiac signals from intra-cardiac leads 26, after passing through filter blocks 48, may be received by a crosspoint switch array 60. The crosspoint switch array 60 may be implemented either as a solid-state switch or by a set of interconnected electromechanical relays and provides multiple electrically independent single-pole, multi-throw switches where pairs of poles are connected to differential inputs of differential analog-to-digital converters 62 and the individual throws are each connected to one of the intra-cardiac leads 26 after passing through the filter blocks 48. In this way, the differential signal across arbitrary pairs of the intra-cardiac electrodes 22 may be measured. The control of the crosspoint switch array 60 (the state of each poll) may be also provided by control lines 49 from the controller 50.

The central controller 50 may also control multiple electromechanical relays 52 which may connect upstream from the filter blocks 48 to designated connectors 20 associated with selected intra-cardiac leads 26 that may be used as stimulating electrodes and/or ablating electrodes, respectively. Relays 52 allow a direct connection to be made to these connectors 20 without passing through filter blocks 48. Relays 52 may also be controlled by controller 50 by control lines 49.

The output of the relays 52 may pass, respectively, to an ablation sensor 66 and a stimulation sensor 68 which in turn receive signals from the ablation unit 36 and stimulator 38. The ablation sensor 66 may measure ablation current and voltage, for example, to provide information about the interface between an intra-cardiac electrode 22 used for ablation and the tissue. Such measurements may reveal, for example, the impedance of the connection which may reflect a degree of charring during the ablation process or the initial contact state of the electrode. The ablation sensor 66 may also provide for edge detection to provide an output signal indicating initiation of ablation that may be used for gating or noise suppression techniques. This information is received by one or more analog-to-digital converters 56 in the analog-to-digital converter bank 58.

Likewise stimulation sensor 68 may provide measures of voltage, current, and edge detection, the latter for gating purposes as described above and the former for measuring impedance to ensure proper electrical connection to the heart tissue. Both the ablation sensor 66 and the stimulation sensor 68 may be controlled by controller 50 through control lines 49.

The output of the analog-to-digital converter bank 58 may be provided to a multiplexer/network interface 70 which takes the data from each of the analog-to-digital converters 56 and 62, encoded as to identity of the particular analogto-digital converter 56 or 62, for high-speed transmission on a data bus 72. This data bus 72 is generally connected in star or daisy-chain fashion to all medical devices 14 (shown in FIG. 1) that may receive digital data encoded in a standardized protocol. In this way digital data from multiple surface ECG leads 18 and multiple intra-cardiac leads 26 may be distributed to multiple devices 14 without problems of loading or the need for various distribution amplifiers or complex lead connections, all leading to risk of additional noise introduction or erroneous connections. Suitable protocols for the data bus 72 include, for example, data protocols such as Ethernet or the like.

As shown in FIG. 1, each of the medical devices 38, 36, 34 and 42 receiving data bus 72 may also connect to a control bus 74 received by the controller 50. In this way the medical devices 14 may independently request different data sources from among the surface ECG electrodes 16 and intra-cardiac electrodes 22 and different combinations and filtering of this data, by means of action by the controller 50 through control lines 49. The request process permits particular lead assets such as the intra-cardiac electrodes 22 to be allocated to individual medical devices 14 in cases where multiple uses might conflict (for example, uses that reflect variously data sensing versus ablation or stimulation).

The control bus 74 may also be a communication protocol such as Ethernet. While typically separate from the data bus 72, the control bus 74 and data bus 72 may be combined over a single medium by multiplexing techniques. In some embodiments, the control bus 74 and data bus 72 may be one or more optical fiber channels instead of direct copper connection. The optical fibers or similar optical isolation can eliminated the leakage currents associated with multiple medical host devices relative to the source.

One or more dedicated digital-to-analog converters 76 may attach to the data bus 72 through a demultiplexer 77 to provide an analog output representing the signal from any one of the surface ECG leads 18 or intra-cardiac leads 26 selected by the controller 50 for use with medical devices requiring analog signal output 78, for example, gating applications on imaging devices such as an x-ray machine 40. Alternatively, the digital-to-analog converter 76 may receive a composite signal generated by the controller 50 from data on the data bus 72 arbitrarily combining signals from multiple sources and applying edge detection algorithms to the signals.

The interface 10 may include a right leg drive circuit 90 that communicates with one connector 20 connecting with the Right Leg electrode 16 to provide a current drive to the Right Leg electrode 16 necessary to bring the analog ground reference level of interface 10 to the desired level of the patient 12. In this regard, the right leg drive circuit 90 may receive control bus 49 to determine a RL drive circuit selection. For example, a measure of ground potential of the patient 12 may be made by a combined average of various signals from different electrodes 16 and various filter pole selections could be made in the RL drive circuit 90 with control from the control bus 49.

Figure 3:
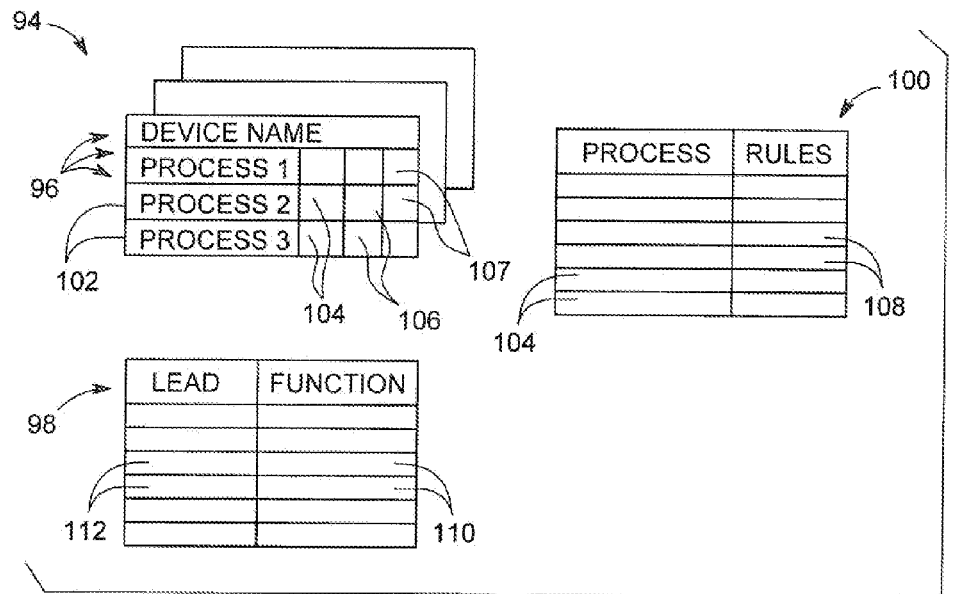
FIG. 3 is a logical representation of several data structures used by the present invention.

The controller 50, in one embodiment, may be a microprocessor or other similar device having at least one processor unit 92 executing a program 95 stored in non-transitory medium of electronic memory 94. Referring also to FIG. 3 the electronic memory 94 may also include various data structures including device files 96, lead function table 98, and process rules table 100. One device file 96 may be associated with each of the medical devices 14 and may describe various processes 102 indicated by rows that may be executed by the associated medical device 14. For example, a stimulator 38 may have different processes that apply different stimulations to different intra-cardiac electrodes 22 or different levels or patterns of stimulation. Each process 102 may provide for a different process type 104 and a different priority 106, the latter which is used in the case of conflicts between medical devices 14 where the medical device 14 with higher priority is able to take access to the particular electrode asset of the surface ECG leads 18 or intra-cardiac leads 26 exclusive of a lower priority device. Each process 102 may also provide for a time duration 107 necessary to complete the process, such as prevents process starvation in other processes as will be described.

The process type 104 may be used to identify an entry in the process rules table 100 which maps process type 104 to a set of procedure rules 108 for that process. The procedure rules 108, for example, may describe the settings of the filter blocks 48, the relays 52, and the crosspoint switch array 60 in implementing that process type 104 and may be prepared by the manufacturer or user of the medical device 14 before use of the coordinating interface 10 or may be prepared dynamically in response to the real-time needs of the medical procedure in process. The procedure rules 108 are used by the central controller 50 in executing the program 95 to generate signals on control lines 49. The procedure rules 108 may further provide operating parameter data, for example, to the controller 50 indicating, for example, desired values from the ablation sensor 66 or stimulation sensor 68 during ablation or pacing, or this information may be passed directly to the medical devices 14 over the data bus 72. Generally, the procedure rules 108 also describe the particular assets or lead types needed for the procedure by their functions. For example, the procedure rules 108 may describe the use of specific surface ECG signals or intra-cardiac signals. For this purpose, lead function table 98 provides a mapping between lead type or function 110 and the actual physical address 112 of the lead, being a location of the relevant connectors 20, determined by the medical personnel connecting the interface 10 to the patient 12. This allows flexibility in connecting particular leads to terminals 20.

Figure 4:
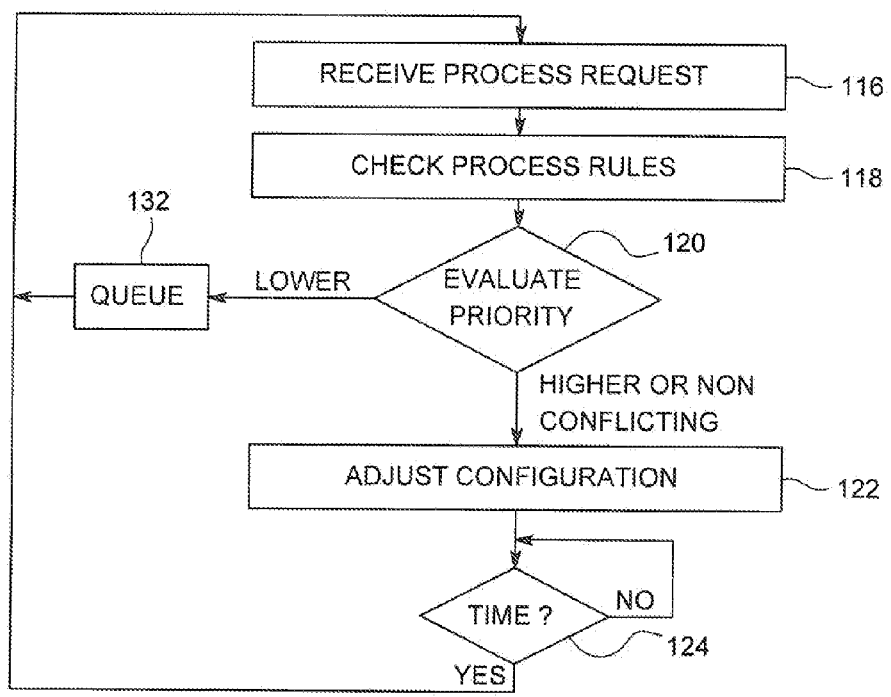
FIG. 4 is a flowchart showing the operation of the present invention in arbitrating requests for limited electrode resources among multiple medical devices.

Referring now to FIG. 4, the program 95 may generally operate to receive and process requests from the medical devices 14 over control bus 74 to the controller 50 as indicated by process block 116. Generally, each request will identify the particular medical device 14 making that request and having an associated device file 96 and one or more processes 102 also identified by the particular request.

At process block 118, the process rules table 100 is analyzed to determine the rules 108 applicable to that process 102 including, for example, the necessary surface ECG leads 18 and intra-cardiac leads 26 and the configurations of the filter blocks 48, crosspoint switch array 60, etc. As noted, the procedure rules 108 may describe the necessary surface ECG leads 18 and intra-cardiac leads 26 in terms of signal function. These particular signal functions may be compared against the lead function table 98 to determine the appropriate terminals 20 and make sure the necessary leads are available. For example, if certain ECG leads are required and are not present in the lead function table 98, an error may be reported to the user. More generally, the lead function table 98 simply provides a mapping for the necessary data.

Assuming the necessary lead assets are available, the priority of the process 102 being requested is determined from the device file 96 and may be evaluated in light of any currently executing processes by other medical devices 14 or pending processes 102 in queue 132 as indicated by decision block 120. Normally each process 102 will have an associated time duration 107, noted above, and in the event that the new requested process 102 has a higher priority than a currently executing process 102, the currently executing process 102 will be allowed to complete its time duration 107. The time duration 107 value may further be set to indefinite to indicate that assets acquired will utilized until explicitly released through removal of the owning process 102 from the device file 96 or removal of the corresponding rule 108. Then, at the conclusion of any executing process 102, the highest priority process 102 in a queue 132 of pending processes 102 or new processes 102 received at process block 116 is allowed to execute next. Pending processes 102 that cannot be executed because of priority are placed in the queue 132 as indicated by the decision branch "lower" of decision block 120.

In one embodiment, the decision block 120 may determine whether the requested process 102 has conflicting resource requirements with pending higher priority processes 102. If not, those two processes 102 may be executed in parallel. For example, two processes 102 that only require the reading of signals from electrodes without inconsistent use of other electrodes may be able to execute concurrently. This determination is made by evaluating the process rules 108 determined at process block 118 against those rules for any ongoing processes 102. In this regard, the process rules 108 for each process 102 may desirably provide a range of acceptable settings, for example, filtration settings, so as to promote the possibility of compatible simultaneous use with other processes 102.

When the process 102 is ready to execute, at process block 122, the necessary configuration is implemented by the central controller 50 and the data is collected and transmitted over the data bus 72. At decision block 124 this process continues for the indicated duration 107 of the process 102 provided by duration 107.

The steps are repeated for each pending process, allowing multiple medical device 14 to share the limited lead resources.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first". "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What we claim is:

1. An interface for electrophysiological signals comprising:
   a set of electrode electrical connectors adapted to connect to electrical leads communicating between a patient and the interface;
   an analog-to-digital converter system providing multiple independent analog-to-digital converters;
   a computer controllable multiway switch connecting signals of the electrical connectors to different inputs of different analog-to-digital converters according to a computer signal for conversion of analog signals from the electrical connectors to digital signals;
   a data network receiving the digital signals and providing connectors adapted to connect the digital signals to medical devices requiring electrical signals from given sets of electrode electrical connectors;
   a control network system receiving requests from at least two given medical devices describing needed electrical signals from the set of electrode electrical connectors; and
   an electronic computer communicating with the control network system and executing a program stored in non-transitory medium to receive the requests from the given medical devices and to arbitrate among the requests to provide the computer signal to the computer controllable multiway switch to connect the given medical devices through the multiway switch to selected electrodes of the set of electrode electrical connectors.

2. The interface for electrophysiological signals of claim 1 wherein at least one of the data network and control network provides a serial communication protocol.

3. The interface for electrophysiological signals of claim 1 wherein at least one of the data network and control network provides an optical fiber link.

4. The interface for electrophysiological signals of claim 1 further including a monitor output connectable to an ECG monitor and receiving output directly from the independent filters without analog-to-digital conversion.

5. The interface for electrophysiological signals of claim 1 further including computer-controllable bypass switches having input terminals connectable to sources of electrical power and outputs connected to ones of the electrode electrical connectors, the computer-controllable bypass switches communicating with the electronic computer to be closed or opened by signals from the electronic computer.

6. The interface for electrophysiological signals of claim 5 wherein the computer-controllable bypass switches are electromechanical relays.

7. The interface for electrophysiological signals of claim 5 further including signal sensors positioned in series along an electrical path between the input terminals connectable to sources of electrical power and those sources of electrical power for providing monitoring signals to the analog-to-digital converter system.

8. The interface for electrophysiological signals of claim 1 further including a right leg drive circuit for providing a drive current to one of the electrode electrical connectors connectable to a ground pad and receiving signals from the data network to determine the drive current.

9. The interface for electrophysiological signals of claim 1 wherein the requests are associated with priorities and an arbitration provides the computer signals according to a priority so that the multiway switch selects the electrodes of the set of electrode electrical connectors required for a request of highest priority.

10. The interface for electrophysiological signals of claim 9 wherein the arbitration allows simultaneous service of requests of different priority that do not require conflicting settings of the multiway switch.

11. The interface for electrophysiological signals of claim 9 wherein the priorities are stored in non-transitory medium indexed to a particular medical device and wherein the requests identify the medical device.

12. The interface for electrophysiological signals of claim 9 wherein the priorities are stored in the non-transitory medium and indexed to a particular process of a particular medical device and wherein the requests identify the medical device and the process of the medical device.

13. The interface for electrophysiological signals of claim 1 wherein the requests identify a particular process and the device data structure stored in non-transitory medium further link processes to process duration and wherein the arbitration grants priority to a given process for the duration in the data structure.

14. The interface for electrophysiological signals of claim 1 wherein the requests identify a particular process and wherein the non-transitory medium holds a configuration data structure linking processes to configurations and wherein the electronic computer executes the program to receive requests identifying particular process and to use the configurations from the configuration data structure to provide the computer signal to the computer controllable multiway switch.

15. The interface for electrophysiological signals of claim 14 wherein the configuration data structure provides configurations identifying a given set of electrode electrical connectors according to functions of associated electrodes and wherein the non-transitory medium further includes a lead function table relating electrode electrical connectors to particular lead functions and wherein the electronic computer executes the program to compare the configurations against lead functions per the lead function table.

16. The interface for electrophysiological signals of claim 15 in which the lead function table includes functions of ECG electrode, intra-cardiac electrode, stimulating electrode, and pacing electrode.

17. The interface for electrophysiological signals of claim 1 further including at least one digital-to-analog converter communicating with the data network to provide an output signal derived from at least one of the signals received by the electrode electrical connectors.

18. The interface for electrophysiological signals of claim 1 further including a multiplexer for multiplexing an output of the independent analog-to-digital converters to the data network.

19. The interface for electrophysiological signals of claim 1 further including a set of electrodes selected from ECG surface electrodes and intra-cardiac electrodes attached to at least some of the electrode electrical connectors.

20. An interface for electrophysiogical signals comprising:
a set of electrode electrical connectors adapted to connect to electrical leads communicating between a patient and the interface;
an analog-to-digital converter system providing multiple independent analog-to-digital converters;
a computer controllable multiway switch connecting signals of the electrical connectors to different inputs of different analog-to-digital converters according to a computer signal for conversion of analog signals from the electrical connectors to digital signals;
a data network receiving the digital signals and providing connectors adapted to connect the digital signals to medical devices requiring electrical signals from given sets of electrode electrical connectors;
a control network system receiving requests from at least two given medical devices describing needed electrical signals from the set of electrode electrical connectors; and
an electronic computer communicating with the control network system and executing a program stored in non-transitory medium to receive the requests from the given medical devices and to arbitrate among the requests to provide the computer signal to the computer controllable multiway switch to connect the given medical devices through the multiway switch to selected electrodes of the set of electrode electrical connectors, further including a computer controllable filter array providing frequency filtering to signals received from the electrode electrical connectors and positioned between the electrode electrical connectors and the analog-to-digital converter system, the computer control filter array communicating with the electronic computer and providing multiple independent filters having frequency profiles selectable by the electronic computer.

21. The interface for electrophysiological signals of claim 20 wherein the multiple independent filters operate in the analog domain.

* * * * *